United States Patent [19]

Wootton et al.

[11] Patent Number: 4,721,720

[45] Date of Patent: Jan. 26, 1988

[54] METHOD OF TREATING EMESIS, ANXIETY AND/OR IBS

[75] Inventors: Gordon Wootton; Gareth J. Sanger, both of Sawbridgeworth, England

[73] Assignee: Beecham Group p.l.c., Brentford

[21] Appl. No.: 838,904

[22] Filed: Mar. 12, 1986

[30] Foreign Application Priority Data

Mar. 14, 1985 [GB] United Kingdom ............... 8506642
Apr. 9, 1985 [GB] United Kingdom ............... 8509039
Dec. 23, 1985 [GB] United Kingdom ............... 8531614

[51] Int. Cl.$^4$ .......................................... A61K 31/44
[52] U.S. Cl. ................................................ 514/304
[58] Field of Search ...................................... 514/304

[56] References Cited

U.S. PATENT DOCUMENTS

4,593,034 6/1986 Munson, Jr. et al. ............... 514/305

FOREIGN PATENT DOCUMENTS

0158265 4/1985 European Pat. Off. .
189002 7/1986 European Pat. Off. .
2100259 5/1982 United Kingdom .
2125398 6/1983 United Kingdom .
2152049 12/1984 United Kingdom .
2153821 1/1985 United Kingdom .
0229444 7/1987 United Kingdom .

OTHER PUBLICATIONS

Florczyk, A. P. et al., *Pharm. Biochem. and Beh.* 14(2), 255–57 (1981).

*Primary Examiner*—Stanley D. Friedman
*Attorney, Agent, or Firm*—James F. Haley, Jr.; Teresa L. Solomon

[57] ABSTRACT

A method of treatment of emesis, anxiety and/or IBS in mammals, including humans, which method comprises administering an effective amount of a compound of formula (I) or (II) or a pharmaceutically acceptable salt thereof:

Ar—Co—Y—Z    (I)

wherein Ar is a group of formula (a):

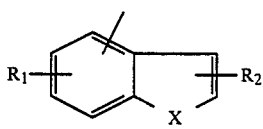

wherein: $R_1$ and $R_2$ are independently selected from hydrogen, halogen, $C_{1-6}$ alkyl, $C_{1-4}$ alkoxy, hydroxy, amino optionally substituted by one or two $C_{1-4}$ alkyl groups, thiol, $C_{1-4}$ alkylthio; X is $CH_2$, $NR_3$, —O— or —S— wherein $R_3$ is hydrogen, $C_{1-4}$ alkyl, $C_{3-5}$ alkenyl, phenyl or phenyl $C_{1-4}$ alkyl; or Ar is a group of formula (b):

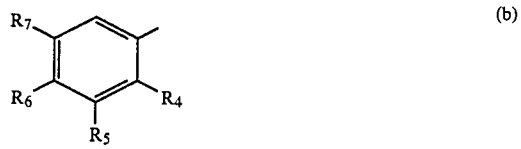

wherein
$R_4$ to $R_7$ are independently hydrogen, halogen, $C_{1-6}$ alkyl, $C_{1-6}$ alkoxy, hydroxy, amino optionally substituted by one or two $C_{1-4}$ alkyl, by $C_{1-4}$ alkanoylamino or pyrrolyl, one of $R_4$ to $R_7$ being other than hydrogen;
Y is —O— or —NH—; and
Z is a group of formula (c), (d) or (e):

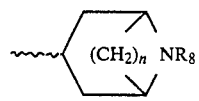

wherein
n is 2, 3 or 4;
$R_8$ is hydrogen, $C_{1-7}$ alkyl, $C_{3-5}$ alkenyl or phenyl $C_{1-4}$ alkyl optionally substituted by one or two halogen, $C_{1-4}$ alkoxy or $C_{1-4}$ alkyl;

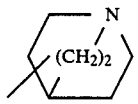

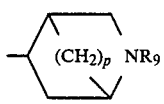

wherein:
p is 1, 2 or 3; and
$R_9$ is as defined above for $R_8$;
and with the proviso that, when Ar is of formula (b) and Y is —NH—, Z is a group of formula (d) or (e);

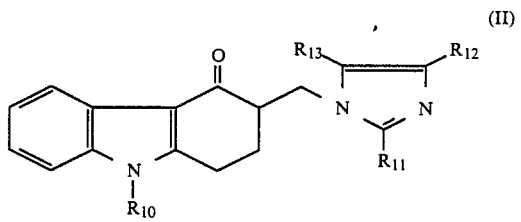

wherein
$R_{10}$ is hydrogen, $C_{1-10}$ alkyl, $C_{3-7}$ cycloalkyl, $C_{3-6}$ alkenyl, phenyl or phenyl-$C_{1-3}$ alkyl; and
one of the groups represented by $R_{11}$, $R_{12}$ and $R_{13}$ is hydrogen, $C_{1-6}$ alkyl, $C_{3-7}$ cycloalkyl, $C_{2-6}$ alkenyl or phenyl-$C_{1-3}$ alkyl and each of the other groups, which may be the same or different, is hydrogen or $C_{1-6}$ alkyl.

12 Claims, No Drawings

METHOD OF TREATING EMESIS, ANXIETY AND/OR IBS

The present invention relates to a method of treatment of emesis, such as cytotoxic agent or radiation induced nausea and vomiting or motion sickness; anxiety; and irritable bowel syndrome (IBS); in mammals including humans, and to the use of compounds in the preparation of a medicament for the treatment of such conditions.

U.K. Patent Applications, Nos. 2100259, 2125398 and 2152049 describe classes of compounds which are aryl amides and esters having an azabicyclic side chain which are 5-HT receptor antagonists useful in the treatment of migraine. U.K. Patent Application No. 2153821 describes a class of tetrahydrocarbazolones which are also 5-HT receptor antagonists.

It has now been discovered that these classes of compounds and related compounds block the emetic response induced by cytotoxic agents such as cisplatin and also by radiation treatment. The compounds are therefore of use in the treatment of nausea and vomiting associated with cancer therapy. The compounds are also of potential use in the treatment of motion sickness, anxiety and irritable bowel syndrome.

Accordingly, the present invention provides a method of treatment of emesis, anxiety and/or IBS in mammals, including humans, which method comprises administering an effective amount of a compound of formula (I) or (II) or a pharmaceutically acceptable salt thereof:

$$Ar\text{—}CO\text{—}Y\text{—}Z \quad (I)$$

wherein Ar is a group of formula (a):

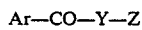

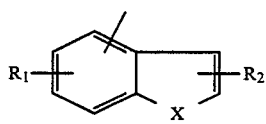
(a)

wherein: $R_1$ and $R_2$ are independently selected from hydrogen, halogen, $C_{1-6}$ alkyl, $C_{1-4}$ alkoxy, hydroxy, amino optionally substituted by one or two $C_{1-4}$ alkyl groups, thiol, $C_{1-4}$ alkylthio; X is $CH_2$, $NR_3$, —O— or —S— wherein $R_3$ is hydrogen, $C_{1-4}$ alkyl, $C_{3-5}$ alkenyl, phenyl or phenyl $C_{1-4}$ alkyl; or Ar is a group of formula (b):

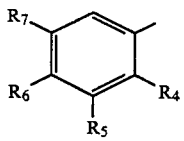
(b)

wherein
$R_4$ to $R_7$ are independently hydrogen, halogen, $C_{1-6}$ alkyl, $C_{1-6}$ alkoxy, hydroxy, amino optionally substituted by one or two $C_{1-4}$ alkyl, by $C_{1-4}$ alkanoylamino or pyrrolyl, one of $R_4$ to $R_7$ being other than hydrogen;
Y is —O— or —NH—; and
Z is a group of formula (c), (d) or (e):

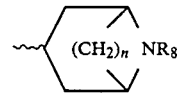
(c)

wherein
n is 2, 3 or 4;
$R_8$ is hydrogen, $C_{1-7}$ alkyl, $C_{3-5}$ alkenyl or phenyl $C_{1-4}$ alkyl optionally substituted by one or two halogen, $C_{1-4}$ alkoxy or $C_{1-4}$ alkyl;

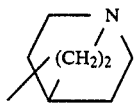
(d)

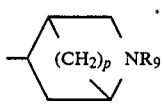
(e)

wherein:
p is 1, 2 or 3; and
$R_9$ is as defined above for $R_8$;
and with the proviso that, when Ar is of formula (b) Y is —NH—, Z is a group of formula (d) or (e);

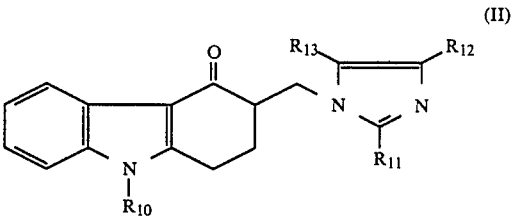
(II)

wherein
$R_{10}$ is hydrogen, $C_{1-10}$ alkyl, $C_{3-7}$ cycloalkyl, $C_{3-6}$ alkenyl, phenyl or phenyl-$C_{1-3}$ alkyl; and
one of the groups represented by $R_{11}$, $R_{12}$ and $R_{13}$ is hydrogen, $C_{1-6}$ alkyl, $C_{3-7}$ cycloalkyl, $C_{2-6}$ alkenyl or phenyl-$C_{1-3}$ alkyl and each of the other groups, which may be the same or different, is hydrogen or $C_{1-6}$ alkyl.

In formula (I):
When Ar is a group of formula (a), suitable values for $R_1$ include hydrogen, chloro, bromo, methoxy, ethoxy, n- and iso-propoxy, amino optionally substituted by one or two methyl groups, thiol, methylthio, ethylthio, n- and iso-propylthio. Preferably $R_1$ is hydrogen.

In the group of formula (a) the carbonyl side chain may be attached to the ring carbon atom in positions 2, 3, 4, 5, 6 or 7 of the nucleus, but preferably in position 3, 4 and 5. Most preferably the carbonyl group is attached to the ring containing X especially in position 3. Preferably X is then $NR_3$ as defined.

$R_1$ is attached to the ring carbon atom in position 4, 5, 6 or 7 of the nucleus, preferably position 5 and $R_2$ is attached to the ring carbon atom in position 2 or 3 of the nucleus. Tautomers are also covered by formula 1 e.g. when $R_2$ is hydroxy or thiol in the 2 position.

$R_3$ is usually hydrogen or alkyl.

When Ar is a group of formula (b) there is a first group of compounds wherein:
$R_4$ is halogen, $C_{1-4}$ alkylamino or $C_{1-4}$ alkoxy;

$R_5$ is hydrogen or halogen;
$R_6$ amino, 4)alkylamino, halogen or 1-pyrrolyl;
$R_7$ is hydrogen or halogen, and preferably $R_6$ is other than hydrogen, halogen or pyrrolyl.

When Ar is a group of formula (b) there is a second preferred group of compounds wherein:

Examples of $R_5$ include halo such as chloro, $C_{1-6}$ alkyl such as methyl, and $C_{1-6}$ alkoxy, such as methoxy, preferably chloro or methyl; examples of $R_6$ include hydrogen, halo, such as chloro, hydroxy, $C_{1-6}$ alkyl such as methyl and $C_{1-6}$ alkoxy, such as methoxy, preferably hydrogen or chloro; examples of $R_7$ include hydrogen, halo such as chloro, $C_{1-6}$ alkyl such as methyl and $C_{1-6}$ alkoxy, such as methoxy, preferably hydrogen, methyl or chloro; $R_4$ is then often hydrogen.

Examples of $R_8$ in formula (c) and $R_9$ in formula (e) when $C_{1-7}$ alkyl include as groups of interest $C_{1-3}$ alkyl such as methyl, ethyl and n- and iso-propyl. Within $C_{1-7}$ alkyl, $C_{4-7}$ alkyl are also of interest, especially those of the formula $(CH_2)uR_{14}$ wherein u is 1 or 2 and $R_{14}$ is a secondary or tertiary $C_{3-6}$ group. Examples of $C_{4-7}$ alkyl include n-, sec- and tert-butyl, n-pentyl, n-heptyl, and iso-butyl, 3-methylbutyl, and tert-butylmethyl. $R_8$ or $R_9$ is preferably methyl.

Examples of $R_8$ or $R_9$ when phenyl $C_{1-4}$ alkyl include benzyl optionally substituted by hydrogen, chloro, bromo, $CF_3$, methoxy, ethoxy, n- or iso-propoxy, methyl, ethyl, n- or iso-propyl.

n is preferably 2 or 3, most preferably 2.

p is often 1 or 2, preferably 2.

In formula (II):

It will be understood that when $R_{10}$ represents a $C_{3-6}$ alkenyl group, the double bond may not be adjacent to the nitrogen atom.

The alkyl groups represented by $R_{10}$, $R_{11}$, $R_{12}$ and $R_{13}$ may be for example, methyl, ethyl, propyl, prop-2-yl, butyl, but-2-yl, methylprop-2-yl, pent-3-yl or hexyl.

An alkenyl group may be, for example, a propenyl group.

A phenyl-$C_{1-3}$ alkyl group may be for example, a benzyl, phenethyl or 3-phenylpropyl group. A cycloalkyl group may be, for example, a cyclopentyl, cyclohexyl or cycloheptyl group.

The pharmaceutically acceptable salts of the compounds of the formula (I) and (II) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) and (II) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) include the compounds quaternised by compounds such as $R_{15}$-T wherein $R_{15}$ is $C_{1-6}$ alkyl, phenyl-$C_{1-6}$ alkyl or $C_{5-7}$ cycloalkyl, and T is a radical corresponding to an anion of an acid. Suitable examples of $R_{15}$ include methyl, ethyl and n- and iso-propyl; and benzyl and phenethyl. Suitable examples of T include halide such as chloride, bromide and iodide.

Examples of pharmaceutically acceptable salts of the compounds of formula (I) also include internal salts such as pharmaceutically acceptable N-oxides.

The compounds of the formula (I) and (II) and, their pharmaceutically acceptable salts may also form pharmaceutically acceptable solvates, such as hydrates, which are included whenever a compound of formula (I) or (II) is herein referred to.

It will of course be realised that some of the compounds of the formula (I) have chiral or prochiral centres, and thus are capable of existing in a number of stereoisomeric forms, including enantiomers. The invention extends to each of these stereoisomeric forms (including enantiomers), and to mixtures thereof (including reacemates). The different stereoisomeric forms may be separated one from the other by the usual methods.

In formula (I) when Z is a group of formula c), Y may be in an exo or endo configuration with respect to the azabicyclic side chain; the endo configuration is preferred.

A group of compounds within formula (I) is of formula (IA):

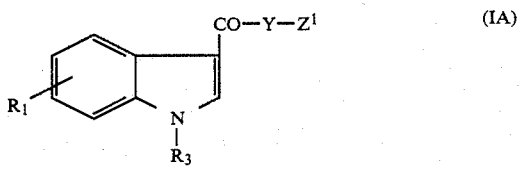

wherein $Z^1$ is a group of formula (c) and the remaining variables are as defined in formula (I).

A further group of compounds within formula (I) is of formula (IB):

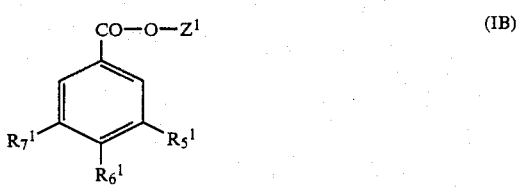

wherein
$R_5^1$ is halo, $C_{1-6}$ alkyl or $C_{1-6}$ alkoxy;
$R_6^1$ is hydrogen or $C_{1-6}$ alkoxy;
$R_7^1$ is halo, $C_{1-6}$ alkyl or $C_{1-6}$ alkoxy; and $Z^1$ is as defined in formula (IA).

There is another group of compounds within formula (I) of formula (IC):

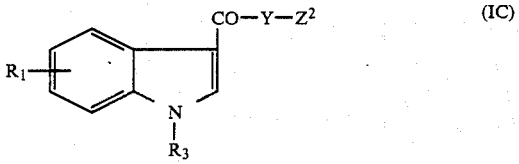

wherein $Z^2$ is a group of formula (d) and the remaining variables are as hereinbefore defined.

There is yet another group of compounds within formula (I) of formula (ID):

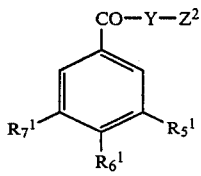
(ID)

wherein the variable groups are as hereinbefore defined.

There is a further group of compounds within formula (I) of formula (IE):

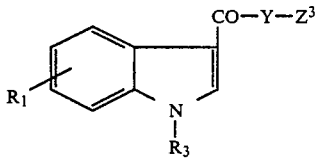
(IE)

wherein $Z^3$ is a group of formula (e) and the remaining variables are as hereinbefore defined.

There is a yet further group of compounds within formula (I) of formula (IF):

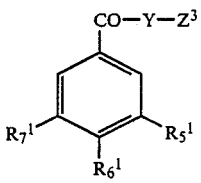
(IF)

wherein the variable groups are as hereinbefore defined.

Suitable and preferred values for the variables in formulae (IA) to (IF) are as described for the corresponding variables under formula (I).

A preferred class of compounds represented by the general formula (II) is that wherein $R_{10}$ represents a hydrogen atom or a $C_{1-6}$ alkyl, $C_{3-6}$ cycloalkyl or $C_{3-6}$ alkenyl group.

Another preferred class of compounds represented by the general formula (II) is that wherein one of the groups represented by $R_{10}$, $R_{11}$ and $R_{12}$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group.

A further preferred class of compounds represented by the general formula (II) is that wherein $R_{10}$ represents a hydrogen atom and $R_{12}$ and $R_{13}$ represents a $C_{1-3}$ alkyl group or $R_{10}$ represents a $C_{1-3}$ alkyl group and both $R_{12}$ and $R_{13}$ represent hydrogen atoms.

A particularly, preferred class of compounds within formula (II) is that represented by the formula (IIA):

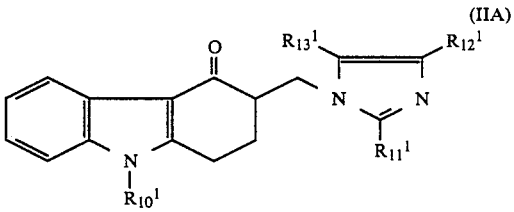
(IIA)

wherein $R_{10}^1$ represents a hydrogen atom or a methyl, ethyl, propyl, prop-2-yl, prop-2-enyl or cyclopentyl group; $R_{12}^1$ represents a hydrogen atom; and either $R_{11}^1$ represents a methyl, ethyl, propyl or prop-2-yl group and $R_{13}^1$ represents a hydrogen atom or $R_{11}^1$ represents a hydrogen atom and $R_{13}^1$ represents a methyl or ethyl group. Preferably $R_{10}^1$ is methyl and $R_{12}^1$ and $R_{13}^1$ are both hydrogen.

Compounds of the formula (I) and (II) may be prepared as described in the aforementioned U.K. patent applications, the subject matter of which are incorporated herein by reference, or by analogous methods thereto.

Examples of cytotoxic agents include those routinely used in cancer chemotherapy, such as cisplatin, doxorubicin, cyclophosphamide, particularly cisplatin.

The administration of the compound of formula (I) or (II), or a pharmaceutically acceptable salt thereof may be by way of oral or parenteral administration.

An amount effective to treat the disorders hereinbefore described depends on the relative efficacies of the compounds of the invention, the nature and severity of the disorder being treated and the weight of the mammal. However, a unit dose for a 70kg adult will normally contain 0.5 to 100 mg for example 1 to 500 mg, of the compound of formula (I) or (II), or a pharmaceutically acceptable salt thereof. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day. No adverse toxicological effects are indicated at any of the aforementioned dosage ranges.

It is preferred that the compound of formula (I) or (II) or a pharmaceutically acceptable salt thereof is administered in the form of a unit dose pharmaceutical composition in which is combined with a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally adminstrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound.

The present invention also provides the use of a compound of formula (I) or (II), or a pharmaceutically acceptable salt thereof in the preparation of a medicament for use in the treatment of emesis, anxiety and/or IBS in mammals, including humans. Such treatment may be carried out in the manner or hereinbefore described.

The present invention further provides a pharmaceutical composition for use in the treatment of emesis, anxiety and/or IBS which comprises an effective amount of a compound of formula (I) or (II), or a pharmaceutically acceptable salt thereof and a pharmaceutically acceptable carrier. Such compositions may be prepared in the manner as hereinbefore described.

The following examples illustrate the preparation of compounds of formula (I) and (II) and the following pharmacological data illustrate the invention.

EXAMPLE 1

3,5-Dichloro-[3α-(8-methyl-8-azabicyclo(3.2.1)octyl)-]benzoate benzoate

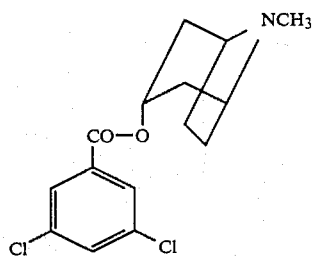

3,5-Dichlorobenzoic acid (4.78 g) was heated at reflux with thionyl chloride (40 ml) in dry benzene (100 ml) for 2hrs. The mixture was evaporated in vacuo. The residue was treated with dry benzene (50 ml) and the mixture was re-evaporated in vacuo. This procedure was carried out three times. An infra-red spectrum of the residue showed complete conversion of the acid to the acid chloride.

Tropine (3.53 g) in dry tetrahydrofuran (50 ml) was cooled in an ice bath and treated dropwise with butyl lithium (15.7 ml; 1.6 M solution in hexane), under nitrogen. The mixture was left at ice-bath temperature for 30 minutes then it was evaporated in vacuo ($<30°$ C.). The residue was treated with dry tetrahydrofuran (50ml) and cooled in an ice-bath.

The acid chloride (prepared above) in dry tetrahydrofuran (30 ml) was added dropwise and the mixture was stirred at room temperature overnight, under nitrogen. The mixture was diluted with dichloromethane and the organic phase was washed with saturated sodium carbonate solution and with brine, dried ($Na_2SO_4$) and evaporated to give a yellow gum (6 g). This was chromatographed on silica gel (120 g) using chloroform, 2% methanol in chloroform, 5% methanol in chloroform then 5% methanol in chloroform containing 0.5% ammonium hydroxide, as successive eluants. The resulting pale yellow solid (3.1 g) was recrystalised from ethyl acetate to give pale yellow crystals (1st crop 1.55 g).

A portion (1.05 g) was dissolved in dry ethanol (1.5 ml) and treated dropwise with ethanolic hydrogen chloride (3.1 ml of 1.1 molar solution). Addition of a few drops of dry ether gave the hydrochloride salt of the title compound as white crystals (970 mg) m.p. 259°–61° C.

m.s. $C_{15}H_{17}NO_2Cl_2$: required: 313.0636: found: 313.0645.

EXAMPLE 2

Indole-[3α-(8-methyl-8-azabicyclo(3.2.1)octyl)]-3-carboxylate

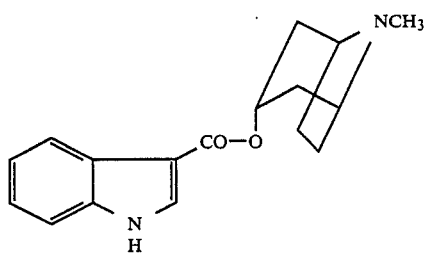

Tropine (6.35 g) in dry tetrahydrofuran (20 ml) was cooled in an ice-bath and treated dropwise with butyl lithium (21.3 ml of 1.6M solution in hexane). The mixture was stirred for 30 minutes at ice-bath temperature then it was evaporated in vacuo (<30° C.). The residue was treated with dry tetrahydrofuran (40 ml) and cooled in an ice-bath.

Indole-3-carboxylic acid chloride [prepared from 5 g of acid as in Example 1]in dry tetrahydrofuran (20 ml) was added dropwise and the resulting mixture was stirred at room temperature, under nitrogen, overnight. The mixture was diluted with dichloromethane and the organic phase was washed with saturated potassium carbonate and with brine, dried ($Na_2SO_4$) and evaporated to give a yellow solid (8.1 g). This was chromatographed on silica gel (250g) using dichloromethane/methanol/ammonium hydroxide (90/10/0.25) then (90/10/0.5) as eluants to give a white solid (3.93 g). A portion (2.93 g) was recrystallised from ethyl acetate to give the title compound (1.57 g) as white crystals. m.p. 199°–202° C. $C_{17}H_{20}N_2O_2$ required: C, 71.81; H, 7.09; N, 9.85%.

found: C, 71.74; H, 7.16; N, 9.75%.

EXAMPLE 3

3,5-Diomethyl-[3α-(8-methyl-8-azabicyclo(3.2.1)octyl)]-benzoate hydrochloride

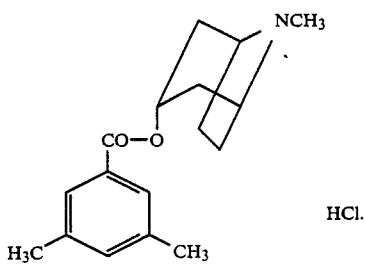

The title compound was prepared in an analogous manner to the compound of Example 1. m.p 250°–252° C.

EXAMPLE 4

Indole-[5-(2-methyl-2-azabicyclo(2.2.2)octyl)]-3-carboxylate carboxylate

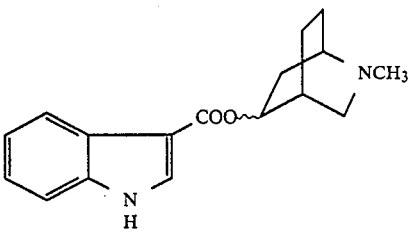

Indole 3-carboxylic acid (913 mg) was stirred overnight with thionyl chloride (10 ml), at room temperature. The excess thionyl chloride was evaporated in vacuo (<30° C.) and the residue was washed with dry ether (3×50 ml).

Meanwhile, 2-methyl-2-azabicyclo(2.2.2)octan-5-ol (800 mg) in dry tetrahydrofuran (5 ml) at 20° C. was treated dropwise with butyl lithium (3.5 ml of 1.6M solution in hexane), under nitrogen. The mixture was stirred 30 minutes at ice-bath temperature then the hexane was evaporated in vacuo. The residue was suspended in dry tetrahydrofuran (20 ml) and the acid chloride (prepared above) in dry tetrahydrofuran (5 ml) was added dropwise. The resulting mixture was stirred at room temperature, under nitrogen, overnight.

The mixture was diluted with dichloromethane and the organic phase was washed with saturated potassium carbonate solution and with brine, dried ($Na_2SO_4$) and evaporated to give a yellow gum (970 mg). This was chromatographed on silica getl (20 g) using dichloromethane, 2% methanol in dichloromethane, 5% methanol in dichloromethane then 5% methanol in dichloromethane containing 0.5% ammonium hydroxide as successive eluants to give the title compound (250 mg) as a white solid.

EXAMPLE 5

1,2,3,9-tetrahydro-9-methyl-3-[(2-methyl-1H-imidazol-1yl)methyl]-4H-carbazol-4-one

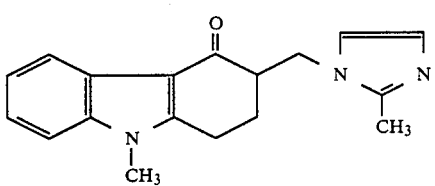

The title compound was prepared in accordance with the procedure described in Example 7 of GB No. 2153821 A m.p. 229°–230° C.

Pharmacological Data

Inhibition of Chemotherapy Induced Nausea and Vomiting

Adult male ferrets (initial body weight 1.3–1.8 kg) were individually housed, fed once daily (200 g Chum Puppy Food plus 50 g Lab Diet A) and were supplied with water ad libitum. Additionally, each animal was given ¼ pint of milk daily during an acclimatization period.

To facilitate intravenous administration of drugs, a chronic indwelling catheter was surgically implanted into the jugular vein using a modification of the technique described by Florczyk and Schurig, 1981 (Pharmacol. Biochem. Behav., 14, 255-257). Prior to surgery each animal was sedated with ketamine hydrochloride (40 mg/animal intramuscularly) and anaesthetised with a halothane-$N_2O$-$O_2$ mixture. A four day recovery period was allowed before commencement of an experiment.

For each group of animals, a preliminary study was carried out to establish an intravenous dose level of cytotoxic agent(s) which would give a consistent and reproducible emetic response. The appropriate dose of example was administered intravenously twice to each animal; 30 minutes before and 30-45 minutes after dosing with cytotoxic agent(s). Running controls received vehicle and cytotoxic agent(s) only.

A single emetic response commenced when an animal assumed a characteristic posture with retching and was concluded when either vomitus was expelled or was present in the mouth as evidenced by a chewing movement. The total number of emetic responses was determined during the four hour period following administration of cytotoxic agent(s) and the number of animals completely protected from emesis determined for each treatment.

All solutions were prepared in water for injection. B.P. Cisplatin was prepared from vials of Neoplatin ™ for injection (Mead Johnson; dose volume of 3 ml/kg). Doxorubicin (Adriamycin ™); Farmitalia Carlo Erba Ltd. Cyclophosphamide (Endoxana ™); W. B. Pharmaceuticals Ltd.

The results obtained are shown below:

| Treatment Dose mg/kg i.v. Administered twice | Dose of Cisplatin mg/kg i.v. | No. of animals completely protected/ No. of animals used |
|---|---|---|
| Vehicle | 10 | 1/11 |
| Compound 1 | | |
| 0.5 | 10 | 3/4 |
| Compound 2 | | |
| 0.005 | 10 | 2/4 |
| 0.05 | 10 | 3/4 |
| 0.5 | 10 | 3/4 |
| Compound 3 | | |
| 0.5 | 10 | 2/3 |

COMPOUNDS 4 and 5

At a treatment dose of 0.5 mg/kg of test compound 16 mg/kg of doxorubicin and 80 mg/kg of cyclophosphamide, the number of animals completely protected was 2/3 and 212 for compounds 4 and 5 respectively.

Other compounds within formulae (I) and (II) as described in UK Patent Applications Nos. 2100259, 2152049, 125398 and 2153821 may be tested and found to be active in the above test.

We claim:

1. A method of treatment of emesis, anxiety and/or IBS in mammals, which method comprises administering to a mammal in need of such treatment an effective amount of a compound of formula (I) or a pharmaceutically acceptable salt thereof:

Ar—CO—Y—I 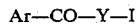 (I)

wherein Ar is a group of formula (a):

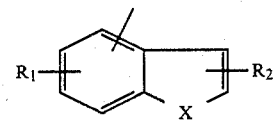

wherein:

$R_1$ and $R_2$ are independently selected from hydrogen, halogen, $C_{1-6}$ alkyl, $C_{1-4}$ alkoxy, hydroxy, amino optionally substituted by one or two $C_{1-4}$ alkyl groups, thiol, $C_{1-4}$ alkylthio; X is $CH_2$, $NR_3$, —O— or —S— wherein $R_3$ is hydrogen $C_{1-4}$ alkyl, $C_{3-5}$ alkenyl, phenyl or phenyl $C_{1-4}$ alkyl;

Y —O— or —NH—; and

Z is a group of formula (c), (d) or (e):

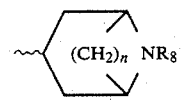

wherein n is 2, 3 or 4;

$R_8$ is hydrogen, $C_{1-7}$ alkyl, $C_{3-5}$ alkenyl or phenyl $C_{1-4}$ alkyl optionally substituted by one or two halogen, $C_{1-4}$ alkoxy or $C_{1-4}$ alkyl;

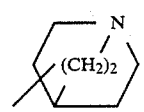

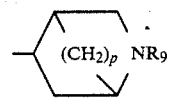

wherein:

P is 1, 2, or 3; and $R_9$ is as defined above for $R_8$.

2. A method according to claim 1 wherein the compound is of formula (I), Ar is of formula (a), and X is $NR_3$ as defined in claim 1.

3. A method according to claim 1 wherein the compound is of formula (IA):

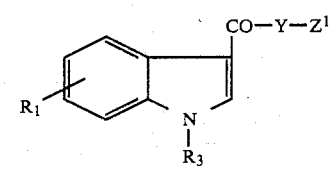

wherein $Z^1$ is a group of formula (c) as defined in claim 1 and $R_1$, $R_3$, and Y are as defined in claim 1.

4. A method according to claim 1 wherein the compound is of formula (IE):

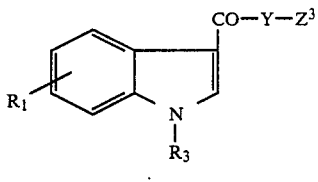

wherein $Z^3$ is a group of formula (e) and $R_1$, $R_3$ and Y are as defined in claim 1.

5. A method according to claim 3 wherein $R_8$ or $R_9$ is methyl or ethyl.

6. A method according to claim 1 wherein the compound of formula (I) is selected from the group consisting of:

3,5-dichloro-[3α-(8-methyl-8-azabicyclo(3.2.1)octyl)]-benzoate, indole-[3α(8-methyl-8-azabicyclo(3.2.1)octyl)]-3-carboxylate, 3,5-dimethyl-[3α-(8-methyl-8-azabicyclo(3.2.1)octyl)]-benzoate, indole-[5-(2-methyl-2-azabicyclo(2.2.2)octyl)]-3-carboxylate, 1,2,3,9-tetrahydro-9-metyl-3-[(2-methyl-1H-imidazol-1-yl)methyl]-4H-carbazol-4-one, or a pharmaceutically acceptable salt of any of the foregoing.

7. A method according to claim 4 wherein $R_8$ or $R_9$ is methyl or ethyl.

8. A method according to claim 1 wherein said mammals are humans.

9. A method of tretatment of emesis, anxiety and/or IBS in mammals, which method comprises administering to a mammal in need of such treatment an effective amount of Indole-[3-(methyl-8-azabicyclo(3.2.1)octyl)]-3-carboxylate.

10. A method of treatment of cytotoxic agent induced nausea and vomiting, which method comprises administering to a mammal in need of such treatment an effective amount of Indole-[3-(methyl-8-azabicylclo (3.2.1) octyl)]-3-carboxylate.

11. A method of treatment of radiation agent induced nausea and vomiting, administering to a mammal in need of such treatment an effective amount of Indole-[3-(methyl-8-azabicyclo(3.2.1)octyl)]-3-carboxylate.

12. A method according to claim 11 wherein the cytotoxic agent is selected from cisplatin, doxorubicin and cyclophosphamide.

* * * * *

UNITED STATES PATENT AND TRADEMARK OFFICE
CERTIFICATE OF CORRECTION

PATENT NO. : 4,721,720

DATED : January 26, 1988

INVENTOR(S) : Gordon Wootton and Gareth John Sanger

Page 1 of 3

It is certified that error appears in the above-identified patent and that said Letters Patent is hereby corrected as shown below:

On the cover page under References Cited, Foreign Patent Documents, "7/1987 United Kingdom" should be -- 7/1987 European Pat. Off. --.

Under ABSTRACT, "Ar-Co-Y-Z" should be -- Ar-CO-Y-Z --.

Column 3, line 2, after "$R_6$" should be -- is hydrogen --.

Column 3, line 2, after "amino," should be -- nitro, --.

Column 3, line 3, "4)alkylamino" should be -- di($C_{1-4}$) alkylamino --.

Column 8, line 5, delete "benzoate".

Column 9, line 50, "3,5-Diomethyl" should be -- 3,5-Dimethyl --.

Column 10, line 46, "lyl)" should be -- 1-yl) --.

UNITED STATES PATENT AND TRADEMARK OFFICE
CERTIFICATE OF CORRECTION

PATENT NO. : 4,721,720
DATED : January 26, 1988
INVENTOR(S) : Gordon Wootton and Gareth John Sanger It is certified that error appears in the above-identified patent and that said Letters Patent is hereby corrected as shown below:

Column 11, line 54, "212" should be -- 2/2 --.

Column 11, line 66, "Ar-CO-Y-I" should be -- Ar-CO-Y-Z --.

Column 12, line 47, "P" should be -- p --.

Column 12, line 49, delete "the com-".

Column 12, line 51, delete "pound is of formula (I), Ar is of formula (a), and".

Column 13, line 17, delete -- 3,5-dichloro-[3α-(8-methyl-8-azabicyclo(3.2.1)octyl]- --.

Column 13, line 18, delete "benzoate,".

Column 13, line 21, delete "3,5-dimethyl-[3α-(8-methyl-8-azabicyclo(3.2.1)octyl)]".

Column 13, line 22, delete "benzoate,".

Column 14, line 1, delete "1,2,3,9-tetrahydro-9-methyl-3-[(2-methyl-1H-imidazol-1-".

Column 14, line 2, delete "yl)methyl]-4H-carbazol-4-one,".

UNITED STATES PATENT AND TRADEMARK OFFICE
CERTIFICATE OF CORRECTION

PATENT NO. : 4,721,720

DATED : January 26, 1988

INVENTOR(S) : Gordon Wootton and Gareth John Sanger

It is certified that error appears in the above-identified patent and that said Letters Patent is hereby corrected as shown below:

Column 14, line 3, delete "any" and substitute therefor -- either --.

Column 14, line 9, delete "anxiety and/or".

Column 14, line 10, delete "IBS".

Column 14, line 12, "Indole" should be -- indole --.

Column 14, line 17, "Indole" should be -- indole--.

Column 14, line 21, "Indole" should be -- indole --.

Column 14, line 23, "claim 11" should be -- claim 10 --.

Signed and Sealed this

Eighth Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.  : 4,721,720
DATED       : January 26, 1988
INVENTOR(S) : Wootton et al.

It is certified that error appears in the above-identified patent and that said Letters Patent is hereby corrected as shown below:

Column 10, line 4, delete "carboxylate".

Column 14, line 12, "Indole-[3-(methyl-8-azabicyclo-(3.2.1)octyl)]-" should be -- indole-[3α-(8-methyl-8-azabicyclo-(3.2.1)octyl)]- --.

Column 14, line 17, "Indole-[3-(methyl-8-azabicyclo-(3.2.1)" should be -- indole-[3α-(8-methyl-8-azabicyclo-(3.2.1) --.

Column 14, line 21, "Indole-[3-" should be -- indole-[3α- --.

Column 14, line 22, "(methyl-8-azabicyclo(3.2.1)-octyl)]-3-carboxylate" should be -- (8-methyl-8-azabicyclo-(3.2.1)octyl)]-3-carboxylate --.

Signed and Sealed this

Fourteenth Day of March, 1989

*Attest:*

DONALD J. QUIGG

*Attesting Officer*   *Commissioner of Patents and Trademarks*

REEXAMINATION CERTIFICATE (1730th)
United States Patent
Wootton et al.

[11] B1 4,721,720
[45] Certificate Issued Jun. 30, 1992

[54] METHOD OF TREATING EMESIS, ANXIETY AND/OR IBS

[75] Inventors: Gordon Wootton; Gareth J. Sanger, both of Sawbridgeworth, England

[73] Assignee: Beecham Group p.l.c.

Reexamination Request:
No. 90/001,951, Feb. 28, 1990

Reexamination Certificate for:
Patent No.: 4,721,720
Issued: Jan. 26, 1988
Appl. No.: 838,904
Filed: Mar. 12, 1986

Certificate of Correction issued Nov. 8, 1988.

[30] Foreign Application Priority Data

Mar. 14, 1985 [GB] United Kingdom ............... 8306842
Apr. 9, 1985 [GB] United Kingdom ............... 8509039
Dec. 23, 1985 [GB] United Kingdom ............... 8531614

[51] Int. Cl.⁵ .................................... A61K 31/44
[52] U.S. Cl. ............................. 514/304; 514/221; 514/305
[58] Field of Search .............................. 514/304

[56] References Cited

U.S. PATENT DOCUMENTS 4,883,803 11/1989 Tyers .................... 514/304

FOREIGN PATENT DOCUMENTS 189002 7/1986 European Pat. Off. .
229444 7/1987 European Pat. Off. .
WO84/03281 8/1984 PCT Int'l Appl. .

Primary Examiner—Stanley J. Friedman
Attorney, Agent, or Firm—James F. Haley, Jr.; Leon R. Yankwich; David K. Barr

[57] ABSTRACT

A method of treatment of emesis, anxiety and/or IBS in mammals, including humans, which method comprises administering an effective amount of a compound of formula (I) or (II) or a pharmaceutically acceptable salt thereof:

$$Ar-CO-Y-Z$$

wherein Ar is a group of formula (a):

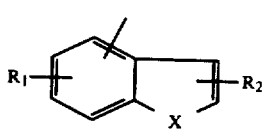

(a)

wherein: $R_1$ and $R_2$ are independently selected from hydrogen, halogen, $C_{1-6}$ alkyl, $C_{1-4}$ alkoxy, hydroxy, amino optionally substituted by one or two $C_{1-4}$ alkyl groups, thiol, $C_{1-4}$ alkylthio; X is $CH_2$, $NR_3$, $-O-$ or $-S-$ wherein $R_3$ is hydrogen, $C_{1-4}$ alkyl, $C_{3-5}$ alkenyl, phenyl or phenyl $C_{1-4}$ alkyl; or Ar is group of formula (b):

(b)

wherein
$R_4$ to $R_7$ are independently hydrogen, halogen, $C_{1-6}$ alkyl, $C_{1-6}$ alkoxy, hydroxy, amino optionally substituted by one or two $C_{1-4}$ alkyl, by $C_{1-4}$ alkanoylamino or pyrrolyl, one of $R_4$ to $R_7$ being other than hydrogen;
Y is $-O-$ or $-NH-$; and
Z is a group of formula (c), (d) or (e):

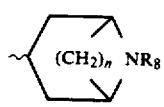

(c)

wherein
n is 2, 3 or 4;
$R_8$ is hydrogen, $C_{1-7}$ alkyl, $C_{3-5}$ alkenyl or phenyl $C_{1-4}$ alkyl optionally substituted by one or two halogen, $C_{1-4}$ alkoxy or $C_{1-4}$ alkyl;

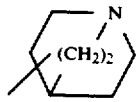

(d)

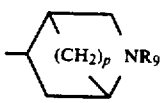

(e)

wherein:
p is 1, 2 or 3; and
$R_9$ is as defined above for $R_8$;

and with the proviso that, when Ar is of formula (b) and Y is $-NH-$, Z is a group of formula (d) or (e);

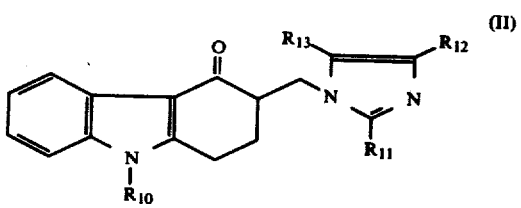

(II)

wherein
$R_{10}$ is hydrogen, $C_{1-10}$ alkyl, $C_{3-7}$ cycloalkyl, $C_{3-6}$ alkenyl, phenyl or phenyl-$C_{1-3}$ alkyl; and
one of the groups represented by $R_{11}$, $R_{12}$ and $R_{13}$ is hydrogen, $C_{1-6}$ alkyl, $C_{3-7}$ cycloalkyl, $C_{2-6}$ alkenyl or phenyl-$C_{1-3}$ alkyl and each of the other groups, which may be the same or different, is hydrogen or $C_{1-6}$ alkyl.

REEXAMINATION CERTIFICATE ISSUED UNDER 35 U.S.C. 307

THE PATENT IS HEREBY AMENDED AS INDICATED ABOVE.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9-12 is confirmed.

Claim 1 is determined to be patentable as amended.

Claims 2-8, dependent on an amended claim, are determined to be patentable.

1. A method of treatment of emesis [, anxiety and/or IBS ] in mammals, which comprises administering to a mammal in need of such treatment an effective amount of a compound of formula (I) or a pharmaceutically acceptable salt thereof:

[AR—CO—Y—     (I)
wherein Ar is a group of formula (a):]

[(a)]

wherein:
$R_1$ and $R_2$ are independently selected from hydrogen, halogen, $C_{1-6}$ alkyl, $C_{1-4}$ alkoxy, hydroxy, amino optionally substituted by one or two $C_{1-4}$ alkyl groups, thiol, $C_{1-4}$-alkylthio; X is $CH_2$, $NR_3$, —O— or —S— wherein $R_3$ is hydrogen, $C_{1-4}$ alkyl, $C_{3-5}$ alkenyl, phenyl or phenyl $C_{1-4}$ alkyl;
Y *is* —O— or —NH—; and
Z is a group of formula (c), (d) or (e):

wherein
n is 2, 3 or 4;
$R_8$ is hydrogen, $C_{1-7}$ alkyl, $C_{3-5}$ alkenyl or phenyl $C_{1-4}$ alkyl optionally substituted by one or two halogen, $C_{1-4}$ alkoxy or $C_{1-4}$ alkyl;

wherein:
P is 1, 2, or 3; and
$R_9$ is as defined above for $R_8$.

* * * * *